United States Patent [19]
Betrabet et al.

[11] Patent Number: 5,618,281
[45] Date of Patent: Apr. 8, 1997

[54] ADHESIVE COMPOSITION COMPRISING A POLYSILOXANE

[75] Inventors: Chinmay S. Betrabet; Yung H. Huang, both of Appleton; Ruth A. Lachapell, Menasha; Lisha Yu, Appleton, all of Wis.

[73] Assignee: Kimberly-Clark Corporation, Neenah, Wis.

[21] Appl. No.: 375,752

[22] Filed: Jan. 20, 1995

[51] Int. Cl.⁶ .................................................. A61F 13/15
[52] U.S. Cl. .......................................... 604/387; 604/385.1
[58] Field of Search ............................... 602/52, 54–56; 604/385.1, 389, 387, 386

[56] References Cited

U.S. PATENT DOCUMENTS

| | | | |
|---|---|---|---|
| 3,645,835 | 2/1972 | Hodgson | 161/146 |
| 3,884,866 | 5/1975 | Jeram et al. | 260/32.8 SB |
| 3,892,707 | 7/1975 | Itoh et al. | 260/37 SB |
| 3,957,704 | 5/1976 | Smith et al. | 260/18 S |
| 3,957,713 | 5/1976 | Jeram et al. | 260/32.8 SB |
| 4,039,707 | 8/1977 | O'Malley | 428/40 |
| 4,072,151 | 2/1978 | Levine | 128/290 R |
| 4,233,978 | 11/1980 | Hickey | 128/295 |
| 4,329,274 | 5/1982 | Faltynek | 524/862 |
| 4,340,709 | 7/1982 | Jeram et al. | 528/15 |
| 4,427,801 | 1/1984 | Sweet | 523/212 |
| 4,563,183 | 1/1986 | Barrodale et al. | 604/329 |
| 4,563,498 | 1/1986 | Lucas | 524/788 |
| 4,631,321 | 12/1986 | Suzuki | 525/478 |
| 4,681,574 | 7/1987 | Eastman | 604/344 |
| 4,683,278 | 7/1987 | Suzuki | 528/32 |
| 4,687,829 | 8/1987 | Chaffee et al. | 528/17 |
| 4,698,406 | 10/1987 | Lo et al. | 528/12 |
| 4,753,648 | 6/1988 | Jackson | 604/389 |
| 4,753,978 | 6/1988 | Jensen | 524/862 |
| 4,822,347 | 4/1989 | MacDougall | 604/329 |
| 4,882,377 | 11/1989 | Sweet et al. | 524/267 |
| 4,989,607 | 2/1991 | Keusch et al. | 128/640 |
| 5,013,307 | 5/1991 | Broida | 604/338 |
| 5,020,547 | 6/1991 | Strock | 128/891 |
| 5,025,073 | 6/1991 | Lewis et al. | 528/15 |
| 5,037,418 | 8/1991 | Kons et al. | 604/387 |
| 5,091,445 | 2/1992 | Revis | 523/212 |
| 5,106,934 | 4/1992 | Wengrovius et al. | 528/15 |
| 5,110,845 | 5/1992 | Gray et al. | 523/211 |
| 5,122,562 | 6/1992 | Jeram et al. | 524/403 |
| 5,203,806 | 4/1993 | Broida | 604/338 |
| 5,214,093 | 5/1993 | Nell et al. | 524/506 |
| 5,246,705 | 9/1993 | Venkatraman et al. | 424/448 |
| 5,292,586 | 3/1994 | Lin et al. | 428/355 |

FOREIGN PATENT DOCUMENTS

| | | |
|---|---|---|
| 0479062A2 | 4/1992 | European Pat. Off. . |
| 0503975A2 | 9/1992 | European Pat. Off. . |
| 0506370A2 | 9/1992 | European Pat. Off. . |
| 6-9622 | 2/1994 | Japan . |
| WO94/01496 | 1/1994 | WIPO . |

OTHER PUBLICATIONS

New Product Information Sheet from Dow Corning Corporation dated 1989 on SYLGARD® Q3-6636 Silicone Dielectric Gel; Form No. 10–349–89.

*Primary Examiner*—David H. Willse
*Assistant Examiner*—Ki Yong O
*Attorney, Agent, or Firm*—John R. Schenian

[57] ABSTRACT

A polysiloxane adhesive composition that is useful in attaching products to human skin. A disposable absorbent product may be prepared that includes the polysiloxane adhesive composition and that may be adhered directly to human skin and peeled off after use with little or no pain to the wearer. In one embodiment, the polysiloxane adhesive composition exhibits a shear storage modulus value, as measured at about 20° C. and at about 10 radians per second, of less than about $1 \times 10^5$ dynes per square centimeter; a hardness value of less than about 5 durometer units (Shore 00), a tan delta value, as measured at about 20° C. and at a frequency of about 10 radians per second, of between about 0.4 to about 2.0; and a maximum peel strength value of between about 35 to about 900 grams of force per 13 millimeters of width, as measured at a peel rate range of 0 to about 5000 millimeters per minute.

11 Claims, 1 Drawing Sheet

ADHESIVE COMPOSITION COMPRISING A POLYSILOXANE

FIELD OF THE INVENTION

The present invention relates to an adhesive composition including a polysiloxane that is useful in attaching products to human skin. More particularly, the invention relates to a disposable absorbent product that includes the adhesive composition and may be adhered directly to human skin and can be peeled off after use with little or no pain to the wearer.

BACKGROUND OF THE INVENTION

Disposable absorbent products currently enjoy widespread use in a large variety of applications. Typical disposable absorbent products include those such as diapers, adult incontinent products, and bed pads, catamenial devices such as sanitary napkins and tampons, and other products such as wipes, bibs, wound dressings, and surgical capes or drapes. Such disposable absorbent products are generally suited to absorb many liquids, such as water or saline, and body liquids such as urine, menses, and blood.

The purpose of disposable absorbent products is typically body waste management. In order to manage liquid body waste, the disposable absorbent product typically includes an absorbent structure that must generally be able to first uptake the liquid into the absorbent structure, then distribute the liquid within the absorbent structure, and then retain the liquid within the absorbent structure.

In order to obtain the desired liquid handling characteristics of the disposable absorbent product, the disposable absorbent product is generally secured to the wearer's body. As an example, securement of a sanitary napkin during use is often accomplished by attaching the sanitary napkin to the wearer's undergarment by a pressure sensitive adhesive. Securing a sanitary napkin to an undergarment can, however, exhibit a number of drawbacks. One drawback is that the adhesive can stick too aggressively to the inside surface of the undergarment leaving residue. Another disadvantage is that the sanitary napkin will tend to move with the undergarment rather than associating with the bodily movements of the wearer. This can result in a less secure fit and increase the incidence of liquid leakage, irritation, chafing and discomfort.

In the past, attempts have been made to adhere a sanitary napkin directly onto a wearer. However, such sanitary napkins have generally had to be relatively large enough so as to avoid the adhesive being placed in contact with the wearer's pubic hair and sensitive genitalia. This is because in securing these sanitary napkins to the wearer, such sanitary napkins generally used adhesives of the type used in various surgical applications. Removal of these adhesives typically causes sudden pain and discomfort to the wearer. Thus, avoiding the sensitive areas of the wearer has been necessary.

It would therefore be desirable to have an adhesive composition that can be used to secure a disposable absorbent product directly to a wearer's body that would be comfortable to wear, would be relatively small and discrete, give the wearer a feeling of security during use, and would not cause discomfort to the wearer upon removal.

SUMMARY OF THE INVENTION

These and other related goals are achieved in the present invention by an adhesive composition that can be used to adhere a disposable absorbent article to human skin and hair, can be peeled off of a wearer with little or no pain, and generally leaves no appreciable residue on the wearer after removal.

One aspect of the present-invention is a pressure sensitive adhesive composition comprising a polysiloxane material that exhibits desired adhesive properties.

In one embodiment of the present invention, a polysiloxane adhesive composition exhibits effective shear storage modulus, hardness, tan delta, and maximum peel strength properties.

In another embodiment of the present invention, a polysiloxane adhesive composition exhibits the following properties:

a) a shear storage modulus value, as measured at about 20° C. and at about 10 radians per second, of less than about $1 \times 10^5$ dynes per square centimeter;

b) a hardness value of less than about 5 durometer units (Shore 00);

c) a tan delta value, as measured at about 20° C. and at a frequency of about 10 radians per second, of between about 0.4 to about 2.0; and d) a maximum peel strength value of between about 35 to about 900 grams of force per 13 millimeters of width, as measured at a peel rate range of 0 to about 5000 millimeters per minute.

In another aspect, it is desirable to provide a disposable absorbent product, such as a sanitary napkin, which disposable absorbent product includes a pressure sensitive adhesive.

In one embodiment, this goal is achieved in a disposable absorbent product comprising a liquid-permeable topsheet, a backsheet, an absorbent structure positioned between the topsheet and the backsheet, at least one major surface adapted to be positioned adjacent a wearer's body, and a pressure sensitive polysiloxane adhesive composition attached to said major surface.

DETAILED DESCRIPTION OF THE PREFERRED EMBODIMENT

Figure 1:
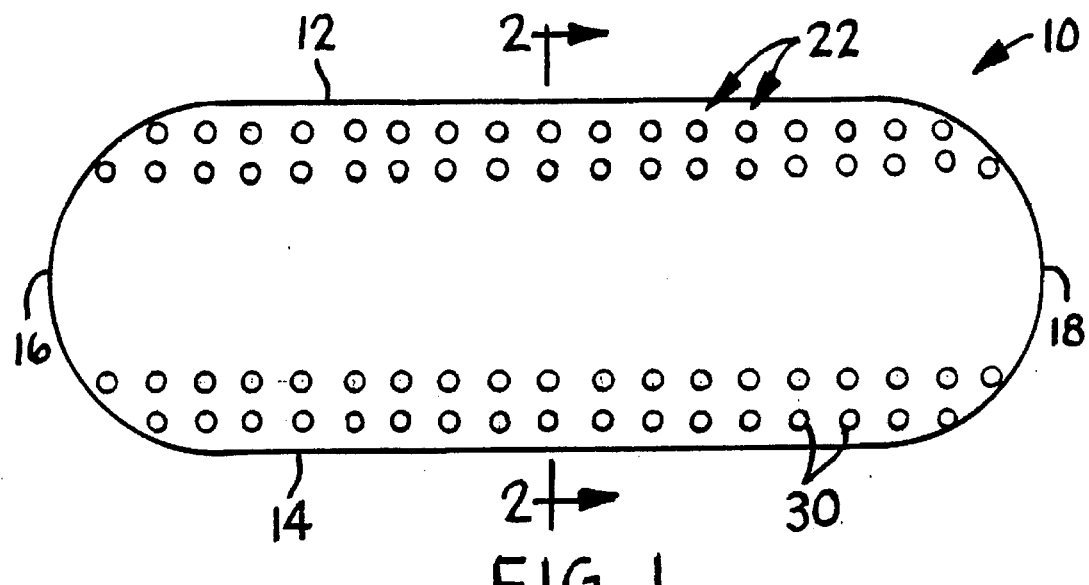
FIG. 1 is a top plan view of one embodiment of a disposable absorbent product according to the present invention.

In one aspect, the present invention concerns a pressure sensitive adhesive composition that possesses improved desirable adhesive properties that may be used to adhere products directly to a human wearer's skin and hair.

As used herein, a "polysiloxane material" is intended to represent a polymeric material that includes alternate silicon and oxygen atoms with hydrogen or various organic groups attached to the silicon.

The pressure sensitive polysiloxane adhesive composition generally may be formed by curing a mixture of a lower alkenyl-functional polysiloxane, such as a vinyl containing polysiloxane, and a hydrogen containing polysiloxane copolymer containing active hydrogen groups. As used herein, the term "active hydrogen groups" is meant to refer to hydrogens which are directly bonded to a silicon atom, such as silicon hydrides and hydrogen containing organopolysiloxanes. The relative amount of each component to be used to prepare the polysiloxane adhesive will be dependent upon such factors as the molar ratio of alkenyl radicals to active hydrogen groups in the uncured composition and the nature of these components, including such variables as polymer chain length, molecular weight, and polymer structure, as well as the adhesive properties desired to be exhibited by the adhesive composition.

Other acceptable methods of inducing crosslinking to prepare the desired polysiloxane adhesive composition include silanol condensation, using organic peroxides, using ultraviolet-initiated crosslinking, using free radical initiated hydrosilation, using high energy radiation crosslinking, or using electron beams.

Starting materials useful in preparing the polysiloxane adhesive composition of the present invention, such as lower alkenyl-functional polysiloxane materials and hydrogen containing polysiloxane copolymer materials containing active hydrogen groups, are well known and may be commercially obtained from such vendors as the Dow Corning Corporation, Wacker Silicones Corporation, and General Electric Corporation.

The components used to prepare the polysiloxane adhesive composition of the present invention can generally be mixed in any manner such as in bulk or in an organic solvent. The polysiloxane adhesive composition can generally be prepared, with or without the aid of an organic solvent, by simply mixing together the desired components in amounts effective to achieve the desired adhesive properties described herein. The order of mixing the materials together is generally not critical. A suitable method of preparing the polysiloxane adhesive composition is achieved by using a two-part component adhesive formulation, wherein one component comprises a lower alkenyl-functional polysiloxane material and the second component comprises a hydrogen containing polysiloxane copolymer material containing active hydrogen groups.

When materials are mixed together to prepare the polysiloxane adhesive composition, the composition generally begins to cure at a rate which is directly proportional to the temperature of the composition. The polysiloxane adhesive composition may generally be cured at room temperature or at an elevated temperature by heating the composition. A suitable temperature for curing the polysiloxane adhesive composition is between about 75° C. to about 250° C.

While the principal components of the adhesive composition of the present invention have been described in the foregoing, such adhesive composition is not limited thereto and can include other components not adversely effecting the desired adhesive properties of the adhesive composition. Exemplary materials which could be used as additional components would include, without limitation, pigments, antioxidants, stabilizers, surfactants, waxes, flow promoters, particulates, inhibitors, catalysts, and accelerators, and materials added to enhance processability of the components.

It has been found that by preparing a polysiloxane material that exhibits the desired adhesive properties described herein, it is possible to prepare a pressure sensitive adhesive that exhibits improved adhesive properties as compared to known adhesive materials.

Adhesive properties desired of the polysiloxane adhesive of the present invention include an effective shear storage modulus value, hardness value, tan delta value, and peel strength value.

As used herein, the term "adhesive" is used to mean that property of any material that allows the material to bond together substrates by surface attachment. Such bonding may result from the application of a pressure force, in the case of a pressure sensitive adhesive material, or a sufficiently high temperature, in the case of a hot-melt adhesive, to contact and bond the adhesive material to a substrate.

The peel strength value of an adhesive material is meant to represent the adhesive bond strength of the material. It is desired that the adhesive material not exhibit a peel strength value that is too high, since such will generally indicate that the adhesive material is too agressive and will, thus, generally cause pain upon removal from a wearer's skin. Also, it is desired that the adhesive material not exhibit a peel strength value that is too low, since such will generally indicate that the adhesive material will generally not effectively remain adhered to a wearer's skin.

Thus, the adhesive composition of the present invention exhibits a maximum peel strength value that is beneficially between about 35 to about 900 grams of force per 13 millimeter width, suitably between about 120 to about 750 grams of force per 13 millimeter width, and more suitably between about 210 to about 360 grams of force per 13 millimeter width, as measured at a peel rate ranging from 0 to about 5000 millimeters per minute and as measured according to the methods described in the Test Methods section herein.

The hardness value of an adhesive material is meant to represent the resistance of the material to deformation. It is desired that the adhesive material not exhibit a hardness value that is too high, since such will generally indicate that the adhesive material is too hard for hair to embed in the adhesive and, thus, will generally not adhere well to a wearer.

Thus, the adhesive composition of the present invention exhibits a hardness value that is beneficially less than about 5 durometer units (Shore 00), suitably less than about 1 durometer unit (Shore 00), and more suitably about 0 durometer units (Shore 00), as measured according to the methods described in the Test Methods section herein.

The tan delta value of an adhesive material is meant to represent the ratio between the shear loss modulus (G") and the shear storage modulus (G') of the material. It is desired that the adhesive material not exhibit a tan delta value that is too high, since such will generally indicate that the adhesive material is too aggressive and will, thus, generally cause pain upon removal from a wearer's skin. Also, it is desired that the adhesive material not exhibit a tan delta value that is too low, since such will generally indicate that the adhesive material exhibits too low of an adhesion and will, thus, generally will not effectively remain adhered to a wearer's skin.

Thus, the adhesive composition of the present invention exhibits a tan delta value that is beneficially between about 0.4 to about 2.0, suitably between about 0.7 to about 2.0, and more suitably between about 0.7 to about 1.5, as measured at about 20° C. and at a frequency of about 10 radians per second, as measured according to the methods described in the Test Methods section herein.

The shear storage modulus value of an adhesive material is meant to represent the flexibility or stretchability of the material. It is desired that the adhesive material not exhibit a shear storage modulus value that is too high, since such will generally indicate that the adhesive material is too inflexible and will, thus, generally be a poor skin adhesive because the adhesive will not conform to a wearer's body movements. It is desired that the adhesive material not exhibit a shear storage modulus value that is too low, since such will generally indicate that the adhesive material lacks sufficient cohesive strength and will, thus, generally break apart and leave residue upon removal from a wearer's skin.

Thus, the adhesive composition of the present invention exhibits a shear storage modulus value that is beneficially less than about $1\times10^5$ dynes per square centimeter, more beneficially between about $1\times10^5$ to about $1\times10^3$ dynes per square centimeter, suitably less than about $7\times10^4$ dynes per square centimeter, and more suitably less than about $2\times10^4$ dynes per square centimeter, as measured at about 20° C. and at about 10 radians per second, as measured according to the methods described in the Test Methods section herein.

The polysiloxane adhesive compositions of the present invention are useful as pressure sensitive adhesives and will readily adhere to a solid support, whether the solid support is flexible or rigid. The polysiloxane adhesive composition may be applied to a solid support surface by any suitable coating means such as rolling, spreading, spraying, and the like, and then subsequently cured as described above.

In another aspect, the present invention relates to a disposable absorbent product comprising a polysiloxane adhesive composition as described herein. The disposable absorbent products according to the present invention are suited to absorb many liquids, such as water, saline, and synthetic urine, and body liquids such as urine, menses, and blood, and are suited for use as diapers, adult incontinent products, and bed pads; in catamenial devices such as sanitary napkins and tampons; and in other disposable absorbent products such as wipes, bibs, wound dressings, and surgical capes or drapes.

The present invention relates generally to disposable absorbent products that are secured to the body of a wearer by a pressure sensitive adhesive. In one embodiment of the present invention, a disposable absorbent product is provided, which disposable absorbent product comprises a liquid-permeable topsheet, a backsheet attached to the topsheet, an absorbent structure positioned between the topsheet and the backsheet, at least one major surface adapted to be positioned adjacent a wearer's body, and a pressure sensitive adhesive composition of the present invention attached to said major surface.

Those skilled in the art will recognize materials suitable for use as the topsheet and backsheet. Examples of materials suitable for use as the topsheet are liquid-permeable materials, such as spunbonded polypropylene or polyethylene having a basis weight of from about 15 to about 25 grams per square meter. Examples of materials suitable for use as the backsheet are liquid-impervious materials, such as polyolefin films, as well as vapor-pervious materials, such as microporous polyolefin films.

While one embodiment of the invention will be described in terms of the use of the adhesive composition of the present invention in a disposable absorbent product such as a sanitary napkin, it is to be understood that the adhesive composition is equally suited for use in other disposable absorbent products known to those skilled in the art. As used herein, the term "sanitary napkin" refers to a product which is worn by females adjacent to the pudendal region and which is intended to absorb and contain various exudates which are discharged from the body, such as, blood, menses and urine. The sanitary napkin is intended to be discarded after a single use. Interlabial devices which reside partially within and partially external of the female wearer's vestibule are also within the scope of this invention.

Figure 2:
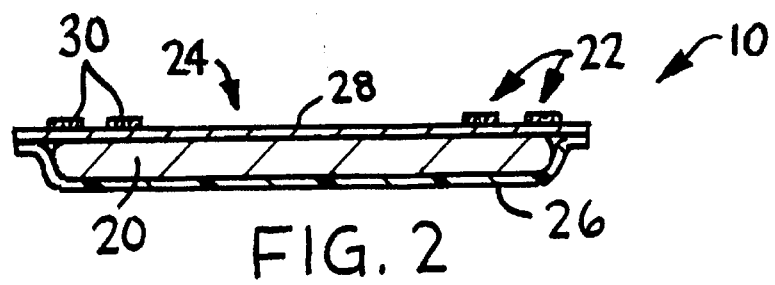
FIG. 2 is a cross-sectional view of FIG. 1 taken along line 2—2.

For ease of understanding when referring to the figures, similar numerals designate like parts in the different views and embodiments. Referring to FIGS. 1 and 2, an embodiment of a sanitary napkin 10 is shown. Although depicted as generally having a race track shape, the sanitary napkin 10 can have any variety of shapes well known to those skilled in the art such as, for example, hourglass, oval, or the like shapes. In the most basic embodiment, the sanitary napkin 10 has a pair of longitudinal sides 12 and 14, transverse ends 16 and 18, an absorbent core 20 and a bodyside adhesive 22. The sanitary napkin 10 has at least one major surface 24 adapted to be positioned adjacent to a wearer's body. That is, the surface 24 is soft and liquid-permeable. Positioned distally from the bodyfacing surface 24 is a fluid-impermeable baffle 26.

The absorbent core 20 may be any material which is generally compressible, comfortable, non-irritating to the wearer's skin and capable of absorbing and containing body exudates such as urine, menses, blood and the like. Desirably, the absorbent core 20 maintains its integrity when wetted during use. The absorbent core 20 can be manufactured into different shapes and from a variety of liquid-absorbent materials commonly known in the disposable absorbent article art. For example, absorbent materials such as cellulose fibers, wood pulp, regenerated cellulose or cotton fibers can be used. Such fibers may be chemically or physically modified. The absorbent core 20 may include any of the above fibers in combination with other materials, both natural and synthetic, such as hydrophilic foams, hydrophilic polymers or the like. Wood pulp is frequently the material of choice primarily because it is inexpensive and readily available. The absorbent core 20 may also include a thin absorbent layer of material such as tissue, fabric or the like made of cellulosic fibers. The absorbent core 20 can also include one or more superabsorbent materials known in the art. By "superabsorbent" we mean a hydrocolloid material that is capable of absorbing an amount of water which is at least ten times the weight of the hydrocolloid particles in the dry form and preferably from about 15 to 70 times the dry weight. Such materials are further described in U.S. Pat. No. 5,247,072 issued on Sep. 21, 1993 to Ning et al. the disclosure of which is incorporated herein and made a part hereof.

The baffle 26 which is typically liquid-impermeable, can be designed to permit the passage of air and moisture vapor to the outer surface while blocking the passage of liquids. The baffle 26 may be made from one or more polymeric films such as polyethylene, polypropylene, cellophane, or a film/nonwoven laminate and the like. The baffle 26 can also be constructed from a liquid-permeable material that has been treated or coated to become liquid impervious.

Referring to FIG. 2, the sanitary napkin 10 includes a liquid-permeable cover 28 having a bodyfacing surface 24. The cover 28 is positioned adjacent to the absorbent core 20. The cover 28, which is designed to contact the wearer's body, can be made from various polymeric films that are apertured for fluid migration into the absorbent core, or from woven or nonwoven fibers or strands produced from natural or synthetic materials which are easily penetrated by body fluids. Thermoplastic polymer films made from polyethylene or polypropylene are preferred. Other acceptable covers might be produced by laminating film and fiber substrates. It can also be beneficial to aperture or emboss (not shown) the cover 28 to increase the rate at which the body fluids can penetrate down and into the absorbent core 20.

The bodyside adhesive 22 is positioned adjacent to the cover 28 in an open, substantially rectangular pattern of small discrete dots or adhesive members 30 so as to leave numerous areas free from adhesive. The adhesive members 30 can have a surface area of about 0.03 square centimeters (cm$^2$) to about 20 cm$^2$ and preferably about 0.15 cm$^2$ to about 15 cm$^2$. As measured from the bodyfacing surface 24 of the cover 28, the adhesive members 30 can have a thickness of about 0.01 millimeters to about 2 millimeters. The dot pattern of FIG. 1 contains approximately the least amount of bodyside adhesive 22 required to obtain sufficient adherence to achieve the desired result and provide a satisfactory removal comfort. Generally, the adhesive 22 is secured to less than about 90 percent of the area of the bodyfacing surface 24, preferably less than about 70 percent of the area and most preferably less than about 20 percent of the area.

It is to be understood that any suitable adhesive pattern may be selected for applying the adhesive 22 to the bodyfacing surface 24 of the sanitary napkin 10, provided it is consistent with the concentration of adhesive 22 desired on the bodyfacing surface 24 yet allowing the sanitary napkin 10 to retain the requisite amount of absorbency. For example, adhesive patterns can be oval, swirls, various linear or non-linear arrays of adhesive longitudinally and/or transversely oriented and reticulated webs having unobstructed interstices between the adhesive fibers or combinations thereof. The adhesive patterns may be open or closed. By "open" it is meant that the adhesive can have an intermittent or continuous pattern that does not substantially cover one or more of the transverse ends 16 and/or 18 of the sanitary napkin 10. By "closed" it is meant that the adhesive would encircle the absorbent core 20. Preferably, the pattern of the adhesive 22 substantially corresponds to the configuration of the absorbent core 20. Desirably, the adhesive 22 is applied in a pattern that is symmetrical about an axis which bisects the sanitary napkin 10 and divides the sanitary napkin 10 into substantially equal portions. This gives the wearer a balanced feel when wearing the sanitary napkin 10. It also reduces the perception of any associated discomfort when the sanitary napkin 10 is removed from the body.

The adhesive 22 can be applied to the bodyfacing surface 24 by techniques known in the art. For example, screen printing or extruding the adhesive 22 from one or more nozzles onto the bodyfacing surface 24 as described in the commonly assigned U.S. Pat. No. 4,995,333 issued to Keller et al. on Feb. 26, 1991, the entire disclosure of which is incorporated herein and made a part hereof.

Disposable absorbent products according to all aspects of the present invention are generally subjected, during use, to multiple insults of a body liquid. Accordingly, the disposable absorbent products are desirably capable of absorbing multiple insults of body liquids in quantities to which the disposable absorbent products will be exposed during use. The insults are generally separated from one another by a period of time.

TEST METHODS:

Peel Strength

The peel strength of an adhesive sample was determined using a modified Pressure Sensitive Tape Council 180° peel resistance test (PSTC-1) described below. PSTC-1 is a standardized test procedure that is described in greater detail on page 23 of the tenth edition of *Test Methods* copyright 1992, available from Pressure Sensitive Tape Council 401 North Michigan Ave., Chicago, Ill. 60611-4267 the disclosure of which is incorporated herein and made a part hereof. The peel strength values were determined according to the following procedure.

A double sided adhesive tape of approximately 13 millimeters wide was secured to the top and bottom edges of a stainless steel test plate having dimensions of about 100 millimeters wide and 152 millimeters long. The adhesive tape was 3M #665 available from the 3M Corporation located in St. Paul, Minn. A polyethylene film 0.05 millimeters thick, male embossed, was secured to the double sided tape with male embossed side as the test surface. The polyethylene film is available from Edison Plastic, located in Washington, Ga. One end of the polypropylene reinforcing film onto which the adhesive sample was molded and cured, i.e. the end that will be the leading end, was rigidly secured to a leading strip of non-stretchable material. The leading strip should be stronger than the peel strength of the adhesive. The test sample was pressed down on the polyethylene film with a 2043 gram mechanical roller, available from Chemsultant International, Mentor, Ohio. The 180° peel was then immediately conducted on a peel strength tester, such as a Materials Test System model 810 available from MTS Corp., Minneapolis, Minn. 55424. When placing the test specimen in the tester, the jaws of the tester were initially set 17.78 cm apart. The steel test panel was secured in the stationary jaw (1.27 cm) with the unsecured leading strip extending past the position of the stationary jaw. The leading strip was then doubled back and clamped in a centered arrangement within the moving jaw of the tester. The tester was activated to conduct the 180° peel test. The moving jaw travelled a total distance of 20.32 cm, with the adhesive tested in the middle 10.16 cm. The peel strength tester can suitably be programed to control the peel rate. As used herein, the peel strength tester was programmed so that the peel rate changed for every 2.03 centimeters of distance traveled by the moving jaw. For the total distance of 20.32 centimeters traveled by the moving jaw, the moving jaw started at a rate of about 100 millimeters per minute and subsequently moved at the respective rates of 300, 500, 700, 900, 1200, 1800, 2500, 3500, and 5000 millimeters per minute. The peel strength with respect to distance traveled is recorded on a chart recorder. The peak of the peel strength/distance curve is taken as being the maximum peel strength in the peel rate range of 0 to about 5000 millimeters per minute.

Hardness

The hardness value of an adhesive sample was measured using a Shore 00 Hardness tester according to ASTM D-2240-91 test method, the contents of which are incorporated in their entirety herein. The hardness tester is available from Shore Instruments Manufacturing company, Freeport, N.Y. The hardness value of an adhesive sample is reported in durometer units, based on the Shore 00 scale.

Rheological Properties

The rheological analysis of an adhesive sample is a method of determining the viscoelastic properties of the adhesive sample. The rheological measurements were obtained by using a Rheometrics Dynamic Spectrometer, model RDS IIE, available from Rheometrics Inc., Piscataway, N.J., by using the procedures recommended in the operating manual, the contents of which is incorporated herein in its entirety. The rheological properties were measured for adhesive samples having a thickness of between about 1 to about 4 millimeters. The adhesive sample was cut into a 25 millimeter diameter circle and placed between two, 25 millimeters diameter parallel plate fixtures of the spectrometer. The upper plate was lowered onto the adhesive sample until a normal force meter indicated a slight deflection. The shear strain applied to the adhesive sample was about 1 percent. The shear storage modulus and the shear loss modulus values for the adhesive sample were measured at about 20° C. and at about 10 radians per second, and is reported in dynes per square centimeter. The tan delta value for the adhesive sample was measured at about 20° C. and at a frequency of about 10 radians per second, and is reported as a dimensionless value.

EXAMPLES:

Polysiloxane adhesive compositions were prepared by hand mixing together various amounts of desired materials. Each polysiloxane adhesive composition was prepared as a 40 gram sample.

For Samples 1–5, 10, and 17, a two-part component adhesive system was used to prepare the polysiloxane adhesive composition. The part-A component of the adhesive system is a clear liquid and exhibits a Brookfield viscosity at about 25° C. of about 3250 centipoise. The part-B component of the adhesive system is a clear liquid and exhibits a Brookfield viscosity at about 25° C. of about 3200 centipoise. The two-part component adhesive system is available from Dow Corning Corporation under the trade designation Sylgard Q3-6636 silicone dielectric gel.

For Sample 1, 3.5 weight parts are used of the part-A component for every 6.5 weight parts used of the part-B component.

For Sample 2, 4 weight parts are used of the part-A component for every 6 weight parts used of the part-B component.

For Sample 3, 4.5 weight parts are used of the part-A component for every 5.5 weight parts used of the part-B component.

For Sample 4, 5 weight parts are used of the part-A component for every 5 weight parts used of the part-B component.

For Sample 5, 5.5 weight parts are used of the part-A component for every 4.5 weight parts used of the part-B component.

For Sample 10, 5.5 weight parts are used of the part-A component for every 5 weight parts used of the part-B component.

For Sample 17, 4.5 weight parts are used of the part-A component for every 6 weight parts used of the part-B component.

For Samples 7, 12, 14, 16, and 18, three materials were used to prepare the polysiloxane adhesive composition. The first material was a crosslinkable polydimethyl siloxane resin system containing trimethylated silica, tetra(trimethyl siloxy) silane, and dimethylvinyl terminated dimethyl siloxane, which is a colorless to pale yellow liquid having a specific gravity at 25° C. of about 1.05, a viscosity of about 35,000 centistokes, and is available from Dow Corning Corporation under the designation Dow Corning 7938 Adhesive. The second material was a noble metal complex catalyst comprising dimethylvinyl terminated polydimethyl siloxane, tetramethyldivinyl disiloxane, and platinum siloxane complex, and is available from Dow Corning Corporation under the trade designation Syl-Off 4000 catalyst. The third material was polydimethylsiloxane fluid having a viscosity of about 100,000 centistokes and is available from Dow Corning Corporation under the trade designation Dow Corning 200 Fluid.

For Sample 7, 10 weight parts were used of the crosslinkable polydimethyl siloxane resin system for every 0.1 weight parts used of the noble metal complex catalyst used. No polydimethylsiloxane fluid was used.

For Sample 12, 36 weight parts were used of the crosslinkable polydimethyl siloxane resin system for every 0.44 weight parts used of the noble metal complex catalyst and 4 weight parts used of the polydimethylsiloxane fluid.

For Sample 14, 38 weight parts were used of the crosslinkable polydimethyl siloxane resin system for every 0.4 weight parts used of the noble metal complex catalyst and 2 weight parts used of the polydimethylsiloxane fluid.

For Sample 16, 39.5 weight parts were used of the crosslinkable polydimethyl siloxane resin system for every 0.4 weight parts used of the noble metal complex catalyst and every 0.6 weight parts used of the polydimethylsiloxane fluid.

For Sample 18, 38.9 weight parts were used of the crosslinkable polydimethyl siloxane resin system for every 0.44 weight parts used of the noble metal complex catalyst and every 1.52 weight parts used of the polydimethylsiloxane fluid.

For Samples 8 and 11, a two-part component system was used to prepare the polysiloxane adhesive composition. The part-A component of the adhesive system is a polydimethylsiloxane mixture including polydimethylsiloxane and methylvinyl polydimethylsiloxane, is a translucent liquid exhibiting a specific gravity of between about 1.04 to about 1.17, and is available from Wacker Silicones Corporation under the designation Elastosil LR 3003/20A US. The part-B component of the adhesive system is a polydimethylsiloxane mixture including polydimethylsiloxane and methylvinyl polydimethylsiloxane, is a translucent liquid exhibiting a specific gravity of between about 1.04 to about 1.18, and is available from Wacker Silicones Corporation under the designation Elastosil LR 3003/20B US.

For Sample 8, 5 weight parts were used of the part-A polydimethylsiloxane mixture for every 5 weight parts used of the part-B polydimethylsiloxane mixture.

For Sample 11, 3 weight parts are used of the part-A polydimethylsiloxane mixture for every 1 weight parts used of the part-B polydimethylsiloxane mixture.

For Samples 13 and 15, a two-part component adhesive system was used to prepare the polysiloxane adhesive composition. The part-A component of the adhesive system is a clear liquid. The part-B component of the adhesive system is a clear liquid. The two-part component adhesive system is available from Dow Corning Corporation under the trade designation Sylgard Q3-6575 silicone dielectric gel.

For Sample 13, 5.5 weight parts are used of the part-A component for every 5 weight parts used of the part-B component.

For Sample 15, 6 weight parts are used of the part-A component for every 4 weight parts used of the part-B component.

For each sample, the described materials in the indicated amounts were hand-mixed together in a small plastic container. A mold was prepared having a length of about 7.5 inches and a width of about 3.5 inches. The mold consisted of a polypropylene reinforcing film, having a thickness of about 0.0015 inch and available from Edison Plastics, Washington, Ga., located between two tetrafluoroethylene fluorocarbon polymer coated sheets, each having a thickness of about 1/16 inch and available from E. I. DuPont de Nemours Co., Wilmington, Del. The top tetrafluoroethylene fluorocarbon polymer coated sheet had two parallel mold cavities, each with a width of about 0.25 inch and a length of about 5 inches and about 2 inches away from the other, through its thickness. Three one-inch binder clips were placed on respective side edges of the assembly to hold the assembly together.

The polysiloxane adhesive sample was then poured into the two mold cavities to the top of the top tetrafluoroethylene fluorocarbon polymer coated sheet, for a thickness of about $\frac{1}{16}$ inch. The mold assembly was then placed in an air-circulating oven at about 123° C. for about 30 minutes. The assembly was then removed from the oven and allowed to cool to room temperature (about 23° C.). The binder clips and the top and bottom tetrafluoroethylene fluorocarbon polymer coated sheets were removed from the adhesive coated polypropylene film. These adhesive coated polypropylene film samples were then used for peel testing. The results of these evaluations are shown in Table 1.

Samples of the polysiloxane adhesive compositions were also prepared for rheological property evaluations. A mold was prepared by cutting a 4 inch by 4 inch square through a tetrafluoroethylene fluorcarbon polymer coated sheet having a length of about 5 inches, a width of about 5 inches, and a thickness of about $\frac{1}{16}$ inch. This mold was supported by another tetrafluoroethylene fluorocarbon polymer coated sheet having similar length, width, and thickness dimensions. The two tetrafluoroethylene fluorocarbon polymer coated sheets were held together using binder clips. The polysiloxane adhesive sample was poured into the mold cavity to the top of the top Teflon-coated sheet, for a thickness of about $\frac{1}{16}$ inch. The mold assembly was then placed in an air-circulating oven at about 123° C. for about 30 minutes. The assembly was then removed from the oven and allowed to cool to room temperature (about 23° C.). The binder clips and the top tetrafluoroethylene fluorocarbon polymer coated sheet were removed from the bottom tetrafluoroethylene fluorocarbon polymer coated sheet. These adhesive sample was then peeled off of the bottom tetrafluoroethylene fluorocarbon polymer coated sheet and then used for rheological testing. The results of these evaluations are shown in Table 1.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

TABLE 1

| Sample Number | Shear Storage Modulus (dynes/cm$^2$) | Tan Delta | Hardness (Shore 00) | Maximum Peel Strength (grams force) |
|---|---|---|---|---|
| 1 | — | — | 12 | 0 |
| 2 | $2.81 \times 10^4$ | 0.35 | 0 | 3 |
| 3 | $2.60 \times 10^4$ | 0.44 | 0 | 6 |
| 4 | $2.11 \times 10^4$ | 0.60 | 0 | 124 |
| 5 | $5.80 \times 10^3$ | 0.82 | 0 | 360 |
| 7 | $2.00 \times 10^5$ | 0.47 | 32 | >1200 |
| 8 | — | — | 65 | 0 |
| 10 | $1.43 \times 10^4$ | 0.77 | 0 | 212 |
| 11 | $1.71 \times 10^5$ | 0.48 | 16 | 35 |
| 12 | $9.36 \times 10^4$ | 0.21 | 15 | 140 |
| 13 | $4.46 \times 10^3$ | 0.15 | 0 | 85 |
| 14 | $1.38 \times 10^5$ | 0.24 | 20 | 365 |
| 15 | $2.20 \times 10^3$ | 0.45 | 0 | 118 |

TABLE 1-continued

| Sample Number | Shear Storage Modulus (dynes/cm$^2$) | Tan Delta | Hardness (Shore 00) | Maximum Peel Strength (grams force) |
|---|---|---|---|---|
| 16 | $8.08 \times 10^4$ | 0.49 | 25 | 898 |
| 17 | $2.36 \times 10^4$ | 0.48 | 0 | 10 |
| 18 | $1.11 \times 10^5$ | 0.43 | 25 | 840 |

We claim:

1. A disposable absorbent product comprising:

i) a liquid permeable topsheet, a backsheet attached to the topsheet, an absorbent structure positioned between the topsheet and the backsheet, and at least one major surface adapted to be positioned adjacent a wearers body; and ii) a polysiloxane adhesive composition attached to said major surface, wherein said polysiloxane adhesive composition comprises the following properties:
   a) a shear storage modulus value, as measured at about 20° C. and at about 10 radians per second, of less than about $1 \times 10^5$ dynes per square centimeter;
   b) a hardness value of less than about 5 durometer units (Shore 00);
   c) a tan delta value, as measured at about 20° C. and at a frequency of about 10 radians per second, of between about 0.4 to about 2.0; and
   d) a maximum peel strength value of between about 35 to about 900 grams of force per 13 millimeters of width, as measured at a peel rate in the range of 0 to about 5000 millimeters per minute.

2. The disposable absorbent product of claim 1 wherein the maximum peel strength value is between about 120 to about 750 grams of force per 13 millimeters of width.

3. The disposable absorbent product of claim 2 wherein the maximum peel strength value is between about 210 to about 360 grams of force per 13 millimeters of width.

4. The disposable absorbent product of claim 1 wherein the hardness value is less than about 1 durometer unit (Shore 00).

5. The disposable absorbent product of claim 4 wherein the hardness value is about 0 durometer units (Shore 00).

6. The disposable absorbent product of claim 1 wherein the tan delta value is between about 0.7 to about 2.0.

7. The disposable absorbent product of claim 6 wherein the tan delta value is between about 0.7 to about 1.5.

8. The disposable absorbent product of claim 1 wherein the shear storage modulus value is between about $1 \times 10^5$ to about $1 \times 10^3$ dynes per square centimeter.

9. The disposable absorbent product of claim 1 wherein the shear storage modulus value is less than about $7 \times 10^4$ dynes per square centimeter.

10. The disposable absorbent product of claim 9 wherein the shear storage modulus value is less than about $2 \times 10^4$ dynes per square centimeter.

11. The disposable absorbent product of claim 1 wherein the polysiloxane adhesive composition is formed by curing a mixture of a lower alkenyl-functional polysiloxane and a hydrogen containing polysiloxane copolymer containing active hydrogen groups.

* * * * *